United States Patent
Ward et al.

(10) Patent No.: US 6,168,022 B1
(45) Date of Patent: Jan. 2, 2001

(54) BABY SUPPLIES CARRYING CASE

(76) Inventors: Ashley H. Ward, 213 Cambridge Ave., Terrace Park, OH (US) 45174; Jane H. Hebert, 4112 Swarthmore St., Houston, TX (US) 77005

(*) Notice: Under 35 U.S.C. 154(b), the term of this patent shall be extended for 0 days.

(21) Appl. No.: 09/047,544

(22) Filed: Mar. 25, 1998

(51) Int. Cl.[7] .................................................. B65D 85/18
(52) U.S. Cl. .......................... 206/581; 206/440; 383/38
(58) Field of Search .................................... 206/233, 278, 206/440, 581; 383/38–40; 604/385.1, 393

(56) References Cited

U.S. PATENT DOCUMENTS

| | | | |
|---|---|---|---|
| 36,710 | * | 10/1862 | Hamlin ..................................... 383/39 |
| 1,688,699 | * | 10/1928 | Gardner, Jr. ............................. 383/38 |
| 2,679,877 | * | 6/1954 | Leggett .................................... 383/39 |
| 2,825,208 | | 3/1958 | Andersen . |
| 4,209,048 | * | 6/1980 | Sandos ................................. 150/132 |
| 4,221,221 | | 9/1980 | Ehlich . |
| 4,702,378 | | 10/1987 | Finkel et al. . |
| 4,738,547 | * | 4/1988 | Brown ..................................... 383/39 |
| 4,852,783 | * | 8/1989 | Bryden et al. ....................... 150/149 |
| 4,964,859 | | 10/1990 | Feldman . |
| 5,002,401 | * | 3/1991 | Blackman .............................. 383/38 |
| 5,020,673 | * | 6/1991 | Adams .................................. 206/581 |
| 5,165,544 | * | 11/1992 | Gusenoff et al. ................. 206/308.3 |
| 5,360,215 | * | 11/1994 | Ruben .................................... 383/38 |
| 5,443,161 | | 8/1995 | Jonese . |
| 5,638,957 | | 6/1997 | Brasler . |
| 5,639,532 | | 6/1997 | Wells . |
| 5,702,379 | | 12/1997 | Preiss . |

* cited by examiner

*Primary Examiner*—Jim Foster
(74) *Attorney, Agent, or Firm*—Harrison & Egbert

(57) ABSTRACT

A baby supplies carrying case including a panel of fabric having a first fold line extending across the panel and a second fold line in spaced parallel relationship to the first fold line. The first fold line and sides of the panel define a first section in the panel. The first and second fold lines and sides of the panel define a second section of the panel. The second fold line and sides of the panel define a third section. The panel is foldable such that the first section overlies the second section. The panel is foldable such that the second section overlies the first section. The third section includes fasteners for maintaining the third section in overlying relationship to the first section. The panel has a first pocket formed therein and located within the first section. The panel has a second pocket opening in the second section and extending into the third section. A third pocket overlies the first pocket and is located within the first section. The first pocket is suitable for receiving a wipe case therein or other similar sized items. The second pocket is suitable for receiving a diaper therein or other similar sized items. A handle is connected to the panel and extends outwardly therefrom so as to allow the case to be suspended from an exterior object.

17 Claims, 4 Drawing Sheets

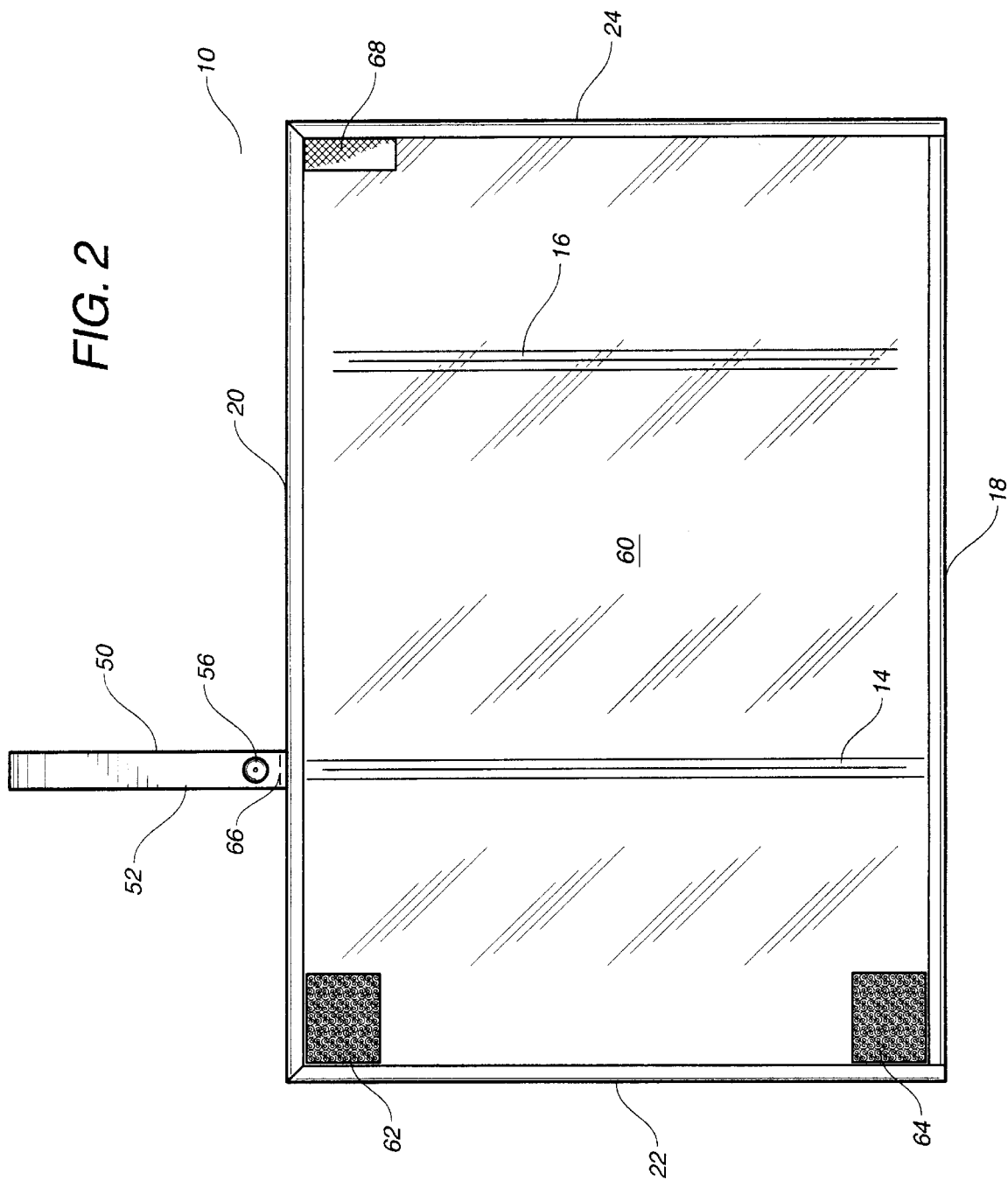

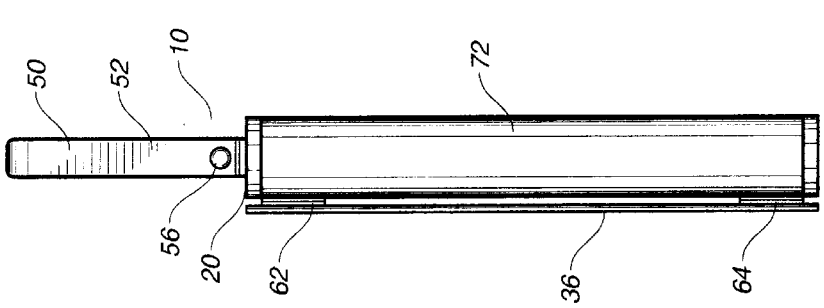
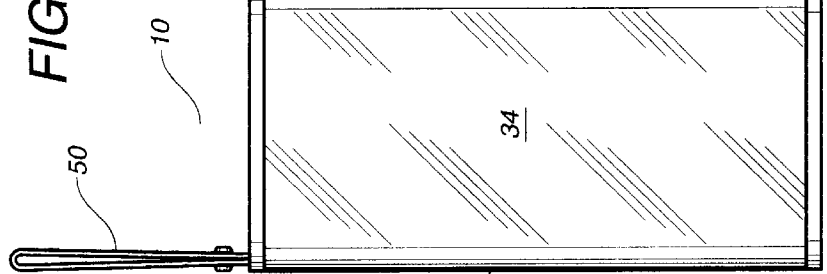
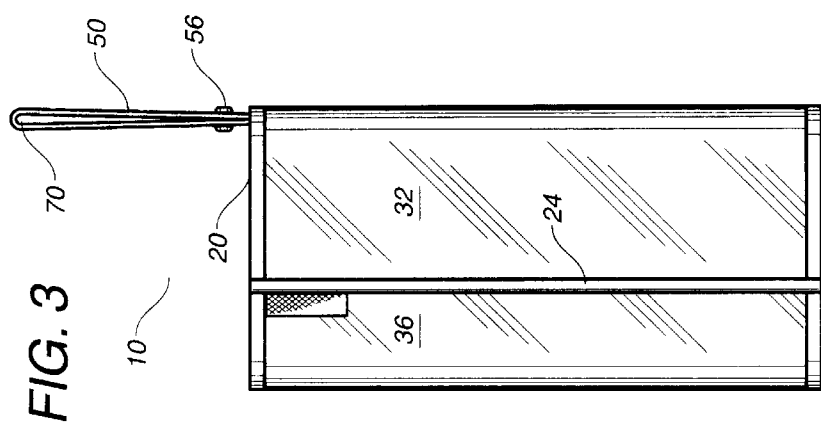
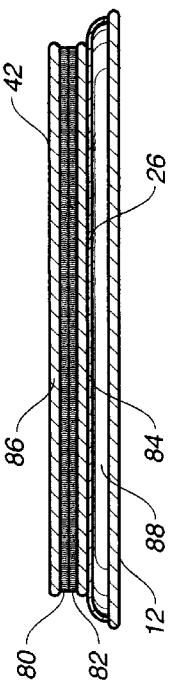
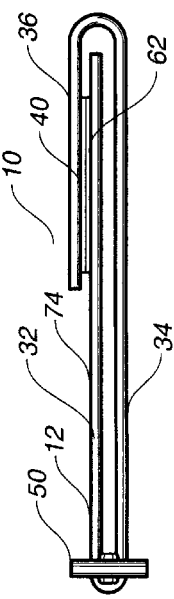

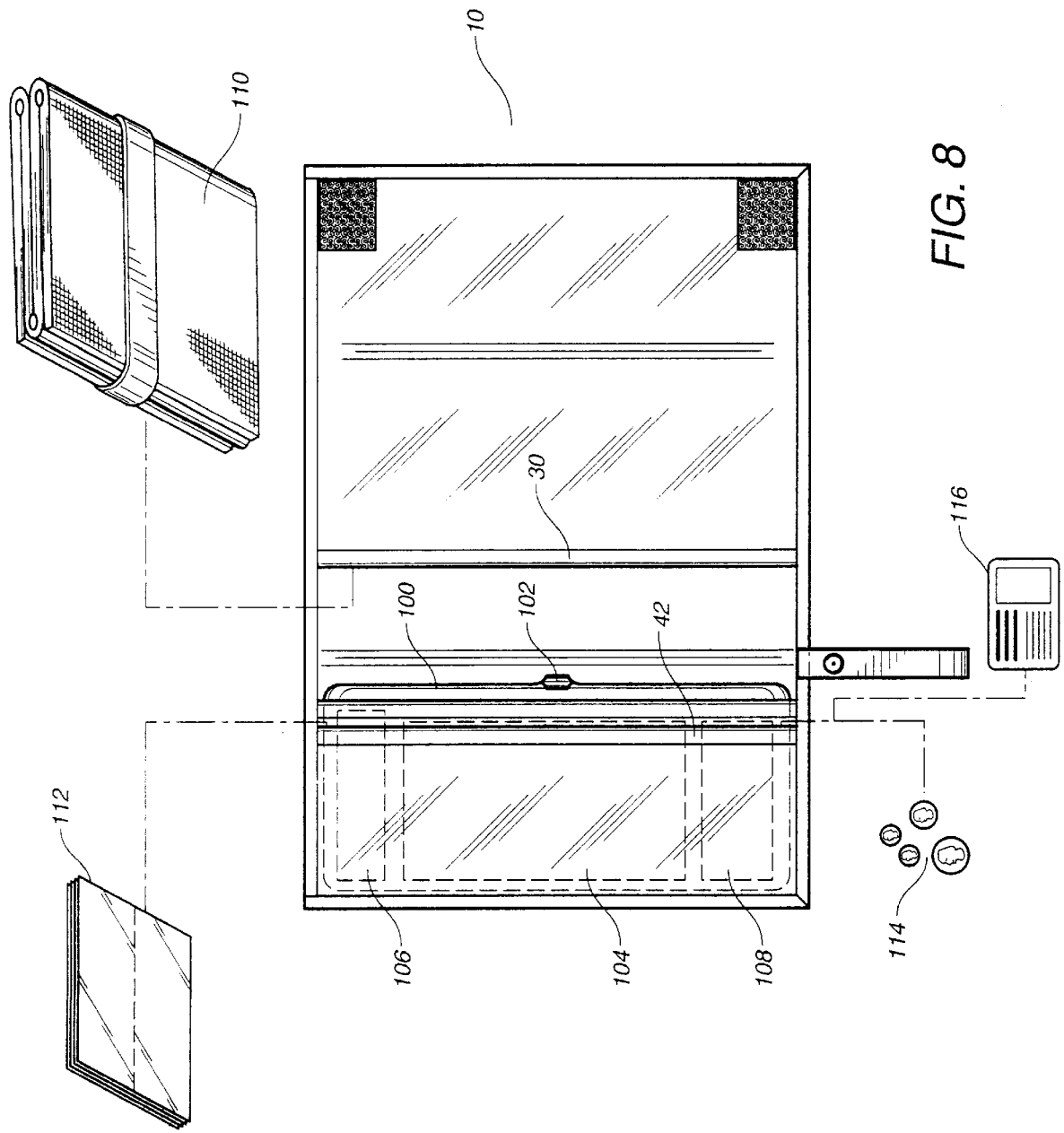

BABY SUPPLIES CARRYING CASE

TECHNICAL FIELD

The present invention relates to devices for the convenient carrying and storage of baby supplies. More particularly, the present invention relates to flexible and foldable cases which are suitable for the receipt of baby supplies.

BACKGROUND ART

Parents and others responsible for infants and small children regularly and in every conceivable location need a reliable supply of both diapers and wipes. This requirement has given rise to numerous devices allowing different baby supplies to be transported.

The most common examples of such an apparatus are standard diaper bags. Diaper bags are typically large, flexible, cloth bags with multiple compartments capable of carrying food, bottles, toys, diapers, wipes, lotions, powders, changing pads and any other accessories needed by a child. While these bags are useful to parents, they have their drawbacks. For example, cloth bags are easily torn, and quickly become dirty from spilled milk, food, and dirty diapers or cloths. Due to the many compartments, it can also be difficult to thoroughly clean the bag.

Additionally, diaper bags are typically so large that at those times where only the essentials of a couple diapers and some wipes are needed, conventional diaper bags become impractical and burdensome. Furthermore, diaper bags tend to cause the diapers to become bunched, rather than keeping them in their original condition, flat and clean.

Additionally, diaper bags are rather unsightly and do not present an attractive appearance to modern professional parents. A need has developed for a convenient way of carrying a small number of diapers and wipes in a sleek and attractive manner.

In the past, various patents have issued on various devices associated with the carrying of baby supplies.

U.S. Pat. No. 2,825,208, issued on Mar. 4, 1958 to D. W. Anderson, describes a refrigerated baby kit which includes a means for equipping a common carrier with articles including milk and food and a refrigerating means therein so that with a baby held in one arm substantially all of the articles required for the baby may be carried by the hand of the other arm. This device is a handbag having a hinged cover with a plurality of elongated bottle retaining pouches or pockets in the underside of the cover and a pouch with a refrigerant.

U.S. Pat. No. 4,221,221, issued on Sep. 9, 1980 to J. L. Ehrlich, describes a utility diaper structure having a plurality of container assemblies connected to a diaper assembly. The diaper assembly has a main body member with a connector assembly for aiding in the connection of the upper edges thereof. The container assemblies are a plurality of sealed members, each of which is releasably connected to the main body member. The container assemblies include a powder packet assembly having a baby powder material sealed within a container member, a towel packet assembly having a towel member sealed within a container member, and a baby oil packet assembly having a baby oil material sealed within a container member.

U.S. Pat. No. 4,702,378, issued on Oct. 27, 1987 to Finkel et al., describes a single use, disposable kit which receives and retains toiletries and a diaper for the care of a baby in a sanitary, tamper-proof fashion. The kit is formed on a thin plastic film that is folded over upon itself so that the toiletries and the diaper are enveloped within the interior of the kit and are protected against degradation.

U.S. Pat. No. 4,964,859, issued on Oct. 23, 1990 to R. L. Feldman, teaches a disposable diaper with an integral changing pad and disposal container forming an integrated changing system for an infant. The disposable diaper has a skin contacting moisture absorbing inner surface and a waterproof environment interfacing outer surface. The changing pad and disposal container are mounted to the outer surface of the diaper and include a liquid impermeable membrane formed so as to define a closeable pocket for retaining a towelette therein in a moistened state.

U.S. Pat. No. 5,638,957, issued on Jun. 17, 1997 to N. Brasier, discloses a reusable diaper and wipe carrying case. The wipe case includes a first housing having an interior surface defining a chamber for holding moistened baby wipes. A second housing has an inner surface defining a chamber for holding diapers. A partition wall is positioned between the access opening of the first housing and the access opening of the second housing. The first housing, the second housing, and the partition wall are hingedly connected at an outside edge so as to permit independent closing and opening to the wipe chamber and diaper chamber.

U.S. Pat. No. 5,639,532, issued on Jun. 17, 1997 to D. R. Wells teaches a cleansing kit composed of a plurality of layers of absorbent tissues laminated together with an inner one of the absorbent layers being impregnated with a cleaning solution and an outer one of the absorbent layers being kept dry by an impermeable plastic middle layer. The inner layer serves to clean a surface being cleaned and the dry outer layer serves to remove any excess cleaner and loosened residual material from the surface after cleaning has been completed.

U.S. Pat. No. 5,702,379, issued on Dec. 30, 1997 to S. Preiss discloses a disposable sanitary article including a first member of an absorbent material, a second member of an impervious material releasably attached to the first member, and at least one third member of impervious material enclosed by the second member. The second member is in the form of a bag. The third member sealingly encloses a cleaning item.

It is an object of the present invention to provide a baby supplies carrying case which is suitable for the receipt of a wipe case and a small number of diapers.

It is another object of the present invention to provide a case which can be folded upon itself in a convenient condition.

It is a further object of the present invention to provide a carrying case that can be unfolded so as to provide a changing surface.

It is a further object of the present invention to provide a case which is reusable.

It is a further object of the present invention to provide a case which can be easily suspended from an exterior object.

It is another object of the present invention to provide a carrying case which is aesthetically pleasing.

It is another object to provide a case that keeps the diapers flat and clean.

It is still a further object of the present invention to provide a carrying case which is easy to use, easy to manufacture, relatively inexpensive, and easy to keep clean.

These and other objects and advantages of the present invention will become apparent from a reading of the attached specification and appended claims.

SUMMARY OF THE INVENTION

The present invention is a baby supplies carrying case that comprises a panel of fabric material having a first fold line extending across the panel and a second fold line in spaced parallel relationship to the first fold line. The first fold line and the sides of the panel define a first section. The first and second fold lines and sides of the panel define a second section. The second fold line and sides of the panel define a third section. The panel is foldable such that the first section overlies the second section. The panel is foldable such that the third section overlies the first section. The third section can be affixed in overlying relationship to the first section so that the panel is in a folded-upon-itself condition. The panel includes a first pocket formed therein and located within the first section. The panel has a second pocket opening in the second section and extending into the third section.

In the present invention, a third pocket overlies the first pocket and is located within the first section. The third pocket includes a complementary strip of hook-and-loop material which is engagable with the strip of hook-and-loop material extending across an exterior surface of the second pocket. The first pocket has an opening which faces the opening of the second pocket. The first and second pockets are formed on an inner surface of the panel.

The means for affixing includes a strip of hook-and-loop material affixed to the inner surface adjacent to the second side edge. A strip of complementary hook-and-loop material is affixed to an outer surface adjacent to the first side edge of the panel. The first pocket opens adjacent to the first fold line. The first pocket extends to the first side edge. The second pocket extends to the second side edge. The panel and the pockets are formed of a liquid-impermeable material, such as NYLON (TM).

In the present invention, a handle is affixed to the panel and extends outwardly therefrom. The handle is a strap having one end affixed to the panel and an opposite end detachably affixed to a surface of the strap such that a loop is formed by the strap.

In the present invention, a wipe case can be releasably received within the first pocket. At least one diaper can be releasably received within the second pocket. The third pocket serves to receive an item from among items such as diaper disposal bags, money, identification cards, driver's licenses and medications.

BRIEF DESCRIPTION OF THE DRAWINGS

FIG. 2 is a plan view of the outer surface of the case of the present invention.

FIG. 3 is a top view showing the case in its folded-upon-itself condition.

FIG. 4 is a bottom view of the case of the present invention in its folded-upon-itself condition.

FIG. 5 is a side view of the case of the present invention in its folded-upon-itself condition.

FIG. 6 is an end view of the case of the present invention in its folded-upon-itself condition.

FIG. 7 is a cross-sectional view taken across line 7—7 of FIG. 1.

FIG. 8 is an exploded view of the case of the present invention showing its receipt of various articles therein.

DETAILED DESCRIPTION OF THE PRESENT INVENTION

Figure 1:
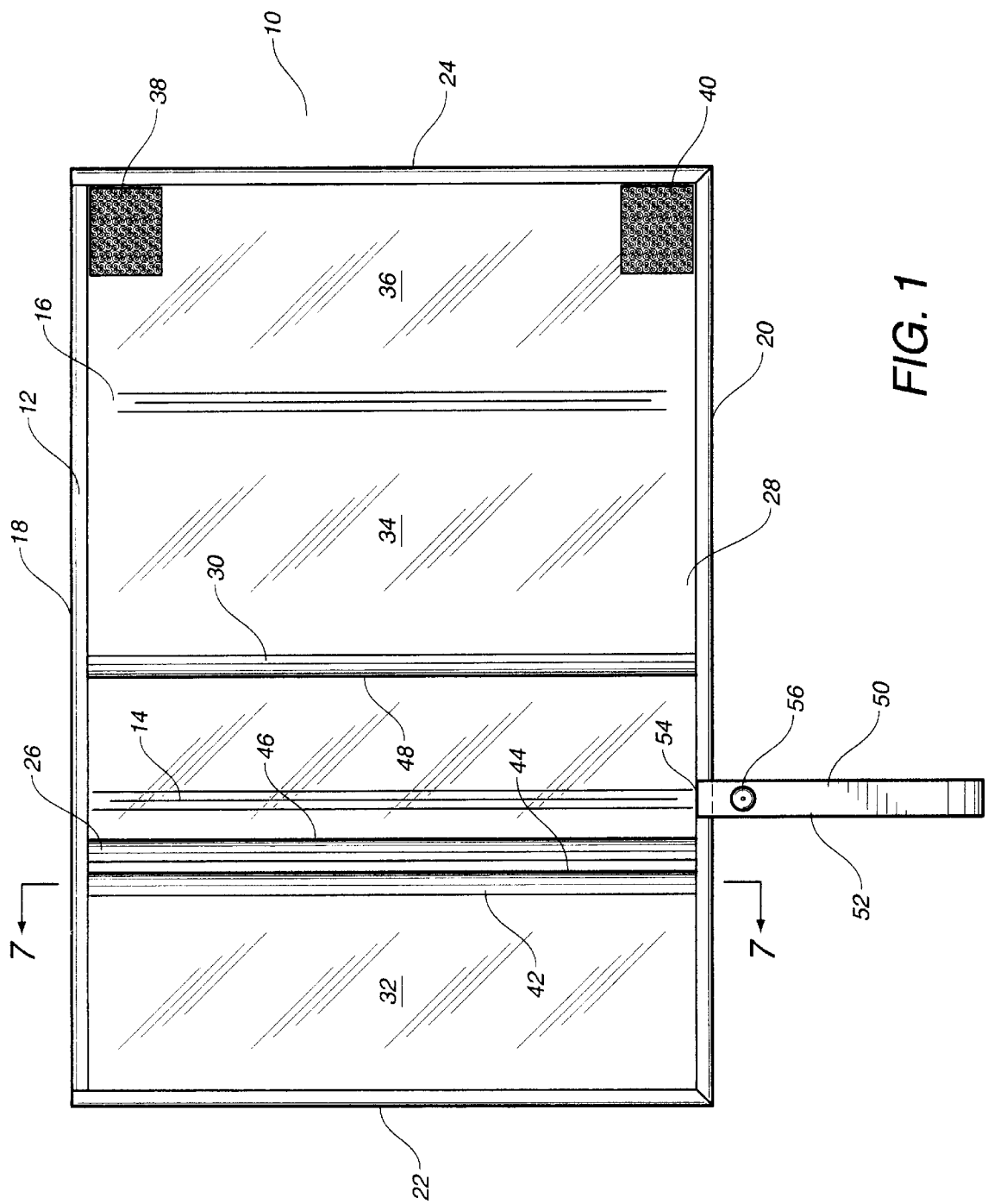
FIG. 1 is a plan view of the inner surface of the case of the present invention.

Referring to FIG. 1, there is shown at 10 the baby supplies carrying case in accordance with the preferred embodiment of the present invention. The carrying case 10 includes a panel 12 of fabric material having a first fold line 14 extending across the panel and a second fold line 16 extending in spaced parallel relationship to the first fold line 14. The panel 12 includes a top edge 18, a bottom edge 20, a first side edge 22 and a second side edge 24. The first fold aine 14 extends from the top edge 18 to the bottom edge 20. The second fold line 16 extends from the top edge 18 to the bottom edge 20. A first pocket 26 is formed on the inner surface 28 of panel 12 adjacent to the first side edge 22. A second pocket 30 is formed on the inner surface 28 of the panel 12.

In the present invention, a first section 32 is defined by the top edge 18, the bottom edge 20, the first side edge 22 and the first fold line 14. A second section 34 is defined by the first fold line 14, the second fold line 16, the top edge 18 and the bottom edge 20. A third section 36 is defined by the top edge 18, the bottom edge 20, the second fold line 16 and the second side edge 24. The first pocket 26 is formed within the first section 32. The second pocket 30 opens in the second section 34 and extends into the third section 36. Strips 38 and 40 of hook-and-loop material are positioned in the corners of the third section 36. The first strip 38 is located in the corner formed between the top edge 18 and the second side edge 24. The second strip 40 is formed in the corner of third section 36 between the bottom edge 20 and the second side edge 24. The strips 38 and 40 suitable for being connected to complementary hook-and-loop material strips found on the outer surface of the first section 32 when the panel 12 is in its folded condition.

The panel 12 is foldable such that the first section 32 will overlie the second section 34. The panel 12 is also foldable such that the third section 36 will overlie the outer surface of the first section 32.

A third pocket 42 will overlie the first pocket 26 within the first section 32. In the preferred embodiment of the present invention, the second pocket 26 will have a strip of hook-and-loop material extending across an exterior surface thereof. The third pocket 42 has an opening adjacent to this strip of hook-and-loop material. The third pocket 42 will have a strip of hook-and-loop material adjacent to the opening of the third pocket 42. The third pocket 42 can thus be fixed in a closed position so as to retain items therein. The third pocket 42 will extend from the opening 44 to the first side edge 22. The first pocket 26 has an opening 46 which faces an opening 48 of the second pocket 30. The first fold line 14 will reside in a position between the openings 46 and 48.

In FIG. 1, it can be seen that the first fold line 14 is located approximately one third of the length of the panel 12 from the first side edge 22. The second fold line 16 is located approximately one quarter of the length of panel 12 from the second side edge 24. As used herein, the term "fold line" can refer to a perforation, a folded area, or to an actual pre-formed fold line. The panel 12, along with the pockets 26, 30 and 42, are formed of liquid-impermeable NYLON (TM) material. As such, any items stored within the pockets should remain dry. Any wet items stored within any of the pockets will be contained so as to avoid leakage therefrom.

In FIG. 1, it can be seen that a handle 50 is affixed to the panel 12 adjacent to the bottom edge 20. Handle 50 is a strap 52 which has one end 54 affixed to the bottom edge 20 of panel 12. A snap-type fastener 56 is formed on the strap 52 so as to releasably receive the opposite end of the strap (shown in other figures).

FIG. 2 shows the outer surface 60 of the carrying case 10 of the present invention. As can be seen in FIG. 2, the outer surface 60 includes its first fold line 14 and the second fold line 16. A first strip 62 of hook-and-loop material is formed at a corner of the outer surface 60 between the first side edge 22 and the top edge 20. A second strip 64 of complementary hook-and-loop material is formed at the corner between the bottom edge 20 and the first side edge 22. The first strip 62 of complementary hook-and-loop material will be detachably received by the first strip 38 of hook-and-loop material. The second strip 64 will be detachably received by the second strip 40.

In FIG. 2, it can be seen that the handle 50 is a strap 52 which has one end 54 connected to the bottom edge 20. An opposite end 66 of strap 52 is joined by snap fastener 56 to the surface of the strap 52. As such, the strap 52 forms a loop. This loop can be connected to exterior items such as handles on a baby carriage, on a hook, on a hanger, or on various other items. The strap facilities holding the case by hand. The strap can be unsnapped from itself to facilitate its secure connection to an exterior item.

In FIG. 2, a label 68 is formed at the corner between the second side edge 24 and the bottom edge 20. Label 68 is indicative of the origin of the carrying case 10 of the present invention.

As used herein, the terms "top edge" and "bottom edge" are used only for descriptive purposes. At any point in time, the "top edge" could be the "bottom edge", and vice versa. Such terms are not intended to be limitative of the scope of the present invention.

FIG. 3 shows the carrying case 10 in its folded-upon-itself condition. As can be seen in FIG. 3, the second side edge 24 of the third section 36 overlies the first section 32. The hook-and-loop fasteners engage each other so that the third section 36 is releasably secured to the top surface of the first section 32. As can be seen in FIG. 3, the handle 50 has an interior loop opening 70. Snap fastener 56 allows the strap to be released from itself.

FIG. 4 shows a back view of the carrying case 10. As can be seen, the second section 34 extends across the back surface. Handle 50 extends upwardly from the edge 72. The various items to be carried are retained within the interior of the carrying case 10.

FIG. 5 is a side view of the folded-upon-itself carrying case 10. FIG. 5 shows that the edge 72 is gently curved so as to accommodate the various items within the interior of the carrying case 10. The strap 50 extends upwardly from the edge 20. A loop is formed by affixing the strap 52 upon itself through the use of the snap-type fastener 56. It can be seen that the third section 36 is secured to the top surface of the first section 32 through the use of the hook-and-loop fasteners 40 and 62 and the hook-and-loop fasteners 38 and 64. The use of the VELCRO (TM) gives the case an adjustable range of thicknesses to accommodate the exact size of the diapers and other items in the case.

FIG. 6 shows the end view of the carrying case 10. In FIG. 6, it can be more clearly seen how the third section 36 overlies the top surface 74 of the first section 32. In particular, it can be seen that the hook-and-loop fastener 40 of the third section 36 engages the complementary hook-and-loop fastener 62 on the first section 32. The first section 32 will overlie the second section 34 in its folded condition. Handle 50 extends outwardly of the panel 12.

In the present invention, the third pocket 42 is affixed to the exterior surface of the first pocket 26 through the use of hook-and-loop fasteners 80 and 82. As can be seen in FIG. 7, hook-and-loop fastener 82 is affixed to the outer surface of the member 84 forming the outer surface of pocket 26.

The complementary hook-and-loop fastener 80 is affixed to the interior surface of the fabric 86 forming the pocket 42. The pocket 26 includes an open interior 88 suitable for the receipt of items therein. Panel 12 forms the backing layer of pocket 26.

FIG. 8 shows the manner in which the pockets of the carrying case 10 of the present invention are suitable for the receipt of various items. It can be seen that the carrying case 10 includes first pocket 26, second pocket 30 and third pocket 42. The first pocket 26 is designed so as to receive an item such as a wipe case 100 therein. Wipe case 100 is a carrying case with a snap-type fastener 102 which allows for the secure storage of items therein or diapers. The wipe case 100 can have a configuration similar to that shown in U.S. Pat. No. 5,638,957. The wipe case 100 can receive premoistened baby wipes 104 (shown in broken line fashion), along with sachets 106 and 108. As such, the premoistened wipes can be carried without drying out. The carrying case 100 can be resupplied, as needed, following use. As used herein, the term "wipe case" can refer to rigid containers of wipes, to foil packs and cases of wipes, and to plastic packets.

The second pocket 30 is configured so as to receive diapers 110 therein or other similar sized items. The pocket 30 should have a suitable size so that a few diapers or other similar sized items can be received therein. The third pocket 42 is a closeable and sealable pocket. Pocket 42 is suitable for the receipt of diaper disposable bags 112, of money 114, of driver's licenses (or identification cards) 116, and of various medications.

When the carrying case 10 of the present invention is in its unfolded condition, the carrying case can double as a changing pad. The arrangement of the pocket 30 keeps the diapers in a flat condition (as opposed to the bunched condition of diapers in a diaper bag). As such, it is easier to change the baby if the diaper is kept in a flat condition. It allows the diapers to be maintained in a clean condition by avoiding exposure to the outside environment. Since the diaper pocket and the wipe case pockets are interchangable, it is possible to avoid the use of the wipe case 102. The pocket 26 can also be used for the storage of an additional diaper. The NYLON (TM) material which is used for the formation of the carrying case 10 is of a very attractive appearance. As such, it will give a sleeker appearance to the user of the carrying case 10.

The foregoing disclosure and description of the invention is illustrative and explanatory thereof. Various changes in the details of the illustrated construction may be made within the scope of the appended claims without departing from the true spirit of the invention. The present invention should only be limited by the following claims and their legal equivalents.

We claim:

1. A baby supplies carrying case comprising:

a panel of fabric material having a first fold line extending across said panel and a second fold line in spaced parallel relationship to said first fold line, said first fold line and sides of said panel defining a first section, said first and second fold lines and sides of said panel defining a second section, said second fold line and sides of said panel defining a third section, said panel foldable such that said first section overlies said second section, said panel foldable such that said third section overlies said first section, said third section having means for affixing in overlying relationship to said first section, said panel having a first pocket formed therein and located within said first section, said panel having a second pocket opening in said second section, said second pocket extending into said third section, a third pocket overlying said first pocket and located within said first section, said second pocket having a strip of hook-and-loop material extending across an exterior surface thereof, said third pocket having an opening adjacent said strip of hook-and-loop material, said third pocket having a strip of complementary hook-and-loop material adjacent said opening of said third pocket.

2. The case of claim 1, said panel having a top edge, a bottom edge, a first side edge extending between said top and bottom edges and a second side edge on an opposite side of said panel from said first side edge, said second side edge extending between said top and bottom edges, said first section defined by said top and bottom edges and said first side edge and said first fold line, said second section defined by said top and bottom edges and by said first and second fold lines, said third section defined by said top and bottom edges and by said second side edge and by said second fold line.

3. The case of claim 2, said first fold line extending from said top edge to said bottom edge, said first fold line located approximately one-third of a length of said panel from said first side edge, said second fold line extending from said top edge to said bottom edge, said second fold line located approximately one-quarter of the length of said panel from said second side edge.

4. The case of claim 2, said panel having an outer surface and an inner surface, said first and second pockets formed on said inner surface of said panel.

5. The case of claim 4, said means for affixing comprising:
a strip of hook-and-loop material affixed to said inner surface adjacent said second side edge; and
a strip of complementary hook-and-loop material affixed to said outer surface adjacent said first side edge.

6. The case of claim 5, said strip of hook-and-loop material comprising:
a first strip of hook-and-loop material positioned in a corner of said inner surface at said top edge and said second side edge; and
a second strip of hook-and-loop material positioned in a corner of said inner surface at said bottom edge and at said second side edge.

7. The case of claim 2, said first pocket opening adjacent to said first fold line, said first pocket extending to said first side edge, said second pocket extending to said second side edge.

8. The case of claim 1, further comprising:
a wipe case releasably received within said first pocket.

9. The case of claim 1, further comprising:
at least one diaper releasably received within said second pocket.

10. The case of claim 1, further comprising:
an item releasably received within said third pocket, said item selected from the group consisting of a diaper disposal bag, money, an identification card, a driver's license and medicine.

11. A baby supplies carrying case comprising:
a panel of fabric material having a first fold line extending across said panel and a second fold line in spaced parallel relationship to said first fold line, said first fold line and sides of said panel defining a first section, said first and second fold lines and sides of said panel defining a second section, said second fold line and sides of said panel defining a third section, said panel foldable such that said first section overlies said second section, said panel foldable such that said third section overlies said first section, said third section having means for affixing in overlying relationship to said first section, said panel having a first pocket formed therein and located within said first section, said panel having a second pocket opening in said second section, said second pocket extending into said third section, said first pocket having an opening facing said opening of said second pocket.

12. A baby supplies carrying case comprising:
a panel of fabric material having a first fold line extending across said panel and a second fold line in spaced parallel relationship to said first fold line, said first fold line and sides of said panel defining a first section, said first and second fold lines and sides of said panel defining a second section, said second fold line and sides of said panel defining a third section, said panel foldable such that said first section overlies said second section, said panel foldable such that said third section overlies said first section, said third section having means for affixing in overlying relationship to said first section, said panel having a first pocket formed therein and located within said first section, said panel having a second pocket opening in said second section, said second pocket extending into said third section; and
a handle affixed to said panel and extending outwardly therefrom, said handle positioned between said first and second pockets.

13. The case of claim 12, said handle comprising:
a strap having one end affixed to said panel, said strap having another end detachably affixed to a surface of said strap such that a loop is formed by said strap.

14. A kit for baby supplies comprising:
a panel of fabric material having a first pocket and a second pocket formed on an inner surface thereof, said panel having a first fold formed between an opening of said first pocket and an opening of said second pocket, said panel having a second fold formed between said opening of said second pocket and a side of said panel, said first and second folds being in parallel spaced relationship;
a wipe case releasably received within said first pocket; and
at least one diaper releasably received within said second pocket.

15. The kit of claim 14, further comprising:
a means for affixing attached to said inner surface of said panel, said means for affixing engageable with a fastener on an outer surface of said panel, said means for affixing for releasably maintaining said panel in a folded-upon-itself condition.

16. The kit of claim 14, further comprising:
a third pocket formed on an exterior surface of said first pocket, said third pocket releasably receiving an item selected from the group consisting of a diaper disposal bag, money, an identification card, a driver's license and a medicine.

17. The kit of claim 14, further comprising:
a strap having one end affixed to said panel, said strap having another end detachably affixed to a surface of said strap such that a loop is formed by said strap.

* * * * *